United States Patent
Shuck

(10) Patent No.: US 9,215,997 B2
(45) Date of Patent: Dec. 22, 2015

(54) IN VIVO TECHNOLOGY SYSTEM FOR HUMAN GUT RESEARCH, DIAGNOSTICS AND TREATMENT

(71) Applicant: L. Zane Shuck, Morgantown, WV (US)

(72) Inventor: L. Zane Shuck, Morgantown, WV (US)

( * ) Notice: Subject to any disclaimer, the term of this patent is extended or adjusted under 35 U.S.C. 154(b) by 71 days.

(21) Appl. No.: 13/931,414

(22) Filed: Jun. 28, 2013

(65) Prior Publication Data

US 2015/0112166 A1 Apr. 23, 2015

Related U.S. Application Data

(63) Continuation-in-part of application No. 13/691,169, filed on Nov. 30, 2012, now Pat. No. 8,491,495.

(51) Int. Cl.
| | |
|---|---|
| *A61B 5/00* | (2006.01) |
| *G09B 23/28* | (2006.01) |
| *A61M 37/00* | (2006.01) |
| *A61B 5/145* | (2006.01) |
| *A61B 1/04* | (2006.01) |
| *A61B 10/00* | (2006.01) |

(52) U.S. Cl.
CPC . *A61B 5/42* (2013.01); *A61B 1/041* (2013.01); *A61B 5/14503* (2013.01); *A61B 10/0038* (2013.01); *A61M 37/00* (2013.01); *G09B 23/28* (2013.01); *A61B 2010/0061* (2013.01)

(58) Field of Classification Search
CPC ........... A61B 5/07; A61B 5/073; A61B 1/041
USPC .................................................. 600/562–584
See application file for complete search history.

(56) References Cited

U.S. PATENT DOCUMENTS

| | | | | |
|---|---|---|---|---|
| 2,881,756 | A * | 4/1959 | Crosby et al. .................. | 600/565 |
| 3,057,344 | A * | 10/1962 | Abella et al. ................... | 600/582 |
| 3,118,439 | A * | 1/1964 | Perrenoud ..................... | 600/582 |
| 3,485,235 | A * | 12/1969 | Felson ........................... | 600/582 |
| 3,528,429 | A * | 9/1970 | Beal et al. ...................... | 600/367 |
| 3,683,890 | A * | 8/1972 | Beal .............................. | 600/371 |
| 3,688,763 | A * | 9/1972 | Cromarty et al. ............. | 600/572 |
| 4,036,214 | A * | 7/1977 | Bucalo .......................... | 600/582 |
| 5,170,801 | A * | 12/1992 | Casper et al. ................. | 600/582 |
| 5,971,942 | A * | 10/1999 | Gu et al. ........................ | 600/582 |
| 7,449,001 | B2 * | 11/2008 | Stoltz ............................ | 600/582 |
| 7,452,338 | B2 * | 11/2008 | Taniguchi ..................... | 600/593 |
| 7,611,480 | B2 * | 11/2009 | Levy ................................ | 604/27 |
| 7,686,770 | B2 * | 3/2010 | Cohen ................ | A61B 10/0266 600/562 |
| 7,717,862 | B2 * | 5/2010 | Stoltz ........................... | 600/582 |
| 7,740,595 | B2 * | 6/2010 | Brown ......................... | 600/565 |
| 7,918,786 | B2 * | 4/2011 | Kawano ............. | A61B 1/00156 600/117 |
| 7,938,775 | B2 * | 5/2011 | Rabinovitz et al. ........... | 600/309 |
| 8,021,356 | B2 * | 9/2011 | Uchiyama et al. ......... | 604/890.1 |
| 8,195,276 | B2 * | 6/2012 | Uchiyama .............. | A61B 1/041 600/424 |
| 8,257,257 | B2 * | 9/2012 | Takizawa ........... | A61B 1/00156 600/101 |
| 8,343,069 | B2 * | 1/2013 | Uchiyama et al. ............ | 600/562 |
| 8,394,034 | B2 * | 3/2013 | Iddan et al. ................... | 600/582 |
| 8,406,490 | B2 * | 3/2013 | Gat et al. ....................... | 382/128 |
| 8,491,495 | B1 | 7/2013 | Shuck | |
| 2001/0051766 | A1 * | 12/2001 | Gazdzinski ................... | 600/309 |
| 2002/0042562 | A1 * | 4/2002 | Meron et al. ................. | 600/361 |
| 2002/0103417 | A1 * | 8/2002 | Gazdzinski ................... | 600/109 |
| 2002/0132226 | A1 * | 9/2002 | Nair et al. ......................... | 435/4 |
| 2003/0020810 | A1 * | 1/2003 | Takizawa et al. .............. | 348/68 |
| 2003/0085994 | A1 * | 5/2003 | Fujita et al. ..................... | 348/77 |
| 2003/0181788 | A1 * | 9/2003 | Yokoi et al. .................. | 600/160 |
| 2003/0208107 | A1 * | 11/2003 | Refael .................. | A61B 1/0008 600/300 |
| 2003/0213495 | A1 * | 11/2003 | Fujita ................. | A61B 1/00059 128/899 |
| 2004/0092825 | A1 * | 5/2004 | Madar et al. .................. | 600/473 |
| 2004/0115877 | A1 * | 6/2004 | Iddan ........................... | 438/200 |
| 2004/0122315 | A1 * | 6/2004 | Krill ............................. | 600/437 |
| 2004/0204630 | A1 * | 10/2004 | Gilad ..................... | A61B 1/041 600/160 |
| 2005/0177069 | A1 * | 8/2005 | Takizawa ............... | A61B 1/041 600/573 |
| 2005/0187433 | A1 * | 8/2005 | Horn ....................... | A61B 1/04 600/160 |
| 2007/0173738 | A1 * | 7/2007 | Stoltz ........................... | 600/582 |
| 2008/0208077 | A1 * | 8/2008 | Iddan ..................... | A61B 1/041 600/582 |
| 2008/0294143 | A1 * | 11/2008 | Tanaka .................. | A61B 1/041 604/506 |
| 2009/0088618 | A1 * | 4/2009 | Arneson .............. | A61B 1/0011 600/373 |
| 2009/0143697 | A1 * | 6/2009 | Tanaka ............... | A61B 1/00158 600/565 |
| 2009/0253999 | A1 * | 10/2009 | Aoki .................. | A61B 1/00016 600/565 |
| 2009/0314106 | A1 * | 12/2009 | van Halsema ... | G01N 33/48764 73/864.91 |
| 2010/0249503 | A1 * | 9/2010 | Yazawa et al. ................ | 600/109 |
| 2010/0331641 | A1 * | 12/2010 | Bangera ................. | A61B 1/041 600/345 |
| 2010/0331827 | A1 * | 12/2010 | Shimizu ................. | A61B 5/073 604/890.1 |
| 2012/0153981 | A1 * | 6/2012 | Arneson et al. .......... | 324/756.01 |
| 2013/0930152 | | 6/2013 | Shuck | |
| 2013/0930558 | | 6/2013 | Shuck | |
| 2013/0204233 | A1 * | 8/2013 | Zou et al. .................... | 604/891.1 |

FOREIGN PATENT DOCUMENTS

JP 05168639 A 7/1993

* cited by examiner

*Primary Examiner* — Michael C Stout

(74) *Attorney, Agent, or Firm* — Birch, Stewart, Kolasch & Birch, LLP

(57) ABSTRACT

A method for diagnosing or treating disease associated with a gut or intestinal tract includes collecting samples of gut microbiota from along an intestinal tract of a patient; perturbing the intestinal tract of the patient; and obtaining a response of the perturbing the intestinal tract of the patient. The method can be implemented using one or more capsules designed for introducing stimuli into the gut or intestinal tract, observing the response to the stimulus, and treating the gut or intestinal tract in view of the response to the stimulus and further in view of acquired empirical data compiled into a database.

24 Claims, No Drawings

IN VIVO TECHNOLOGY SYSTEM FOR HUMAN GUT RESEARCH, DIAGNOSTICS AND TREATMENT

CROSS REFERENCE TO RELATED APPLICATIONS

This application is a continuation-in-part of U.S. application Ser. No. 13/691,169 filed Nov. 30, 2012, now U.S. Pat. No. 8,491,495, which claims the benefit of U.S. application Ser. No. 61/727,177 filed Nov. 16, 2012, the contents of which are incorporated by this reference herein in their entirety.

FIELD OF THE INVENTION

This invention pertains to an in vivo technology based apparatus, process and method involving hybrid bioengineering, biomedical-engineering, general engineering, medical sciences and medical professional disciplines. The field encompasses all those disciplines associated with the processes of the human gut, i.e., the digestion process for the entire GI tract, functions of the gut, dysfunctions, and abnormal behavior of the gut as may be reflected in any number of illnesses and diseases. The relevance, nature, and manner of microbial involvement in the digestive process, and many illnesses and diseases is of particular emphasis, including discovery, isolation, and characterization of heretofore unknown microbe species/strains. Three diverse in vivo tools, referred to generally as Capsules A, B and C, and referred to alternatively from time to time as Inventions I, II and III respectively, comprise a component part of this in vivo System, and form a new comprehensive method and process for holistically exploring, researching, characterizing, diagnosing, and treating the human gut as a longitudinal, distributed, multidisciplinary anatomical-biological system. As opposed to current in vitro methodology, this invented global process is a comprehensive multidisciplinary in vivo basic biological sciences, research, medical-sciences, and bioengineering systems approach to gut science and healthcare.

BACKGROUND OF INVENTION

The heretofore inaccessible regions of the most important anatomy of the gut, and the lack of technology to explore, discover, and experiment in an in vivo manner, and then administer medications and measure in vivo the immediate results, has constrained and obstructed beyond description throughout history the advance of medical science pertaining to the gut. Food suppliers and preparers are largely oblivious to gut responses to the foods they deliver. As an intelligent society, we appear grossly disorganized in this regard, especially as pertains to priorities, such as exploring and knowing more about the cosmos than our own gut. The importance and urgency of such inexplicable phenomena posed an irresistible challenge to formulate a global perspective of the gut as a system and to identify the pertinent variables. It came as a surprise initially to learn that there are more than 10,000 variables, many of which have never been identified or characterized, that affect gut health. Never in history has there been so little known about such a common, popular item manifested in and possessed by all animals.

A competent research effort investigating any animate or inanimate system should attempt to identify the fundamental multidisciplinary scientific principles of science and engineering upon which the system is based and functions, and then develop quantitative measures of those principles. The inaccessibility of the gut, and heretofore lack of technology, has resulted in speculation and statistical correlation of symptoms from a distance throughout history as a means of researching the gut. The need for in vivo technology became immediately apparent. However, as a civilized society we have imposed some extremely limiting constraints and time consuming processes upon the development and implementation of medical technology. The technical challenge alone is formidable. Nevertheless, the only systematic and rational approach to developing gut medical science appears to demand in vivo technology. Likewise, never in our history has there been such a broad-based, compelling need for such technology. Thus, a holistic research perspective was formed and the possible combinations of many tools and processes needed to accomplish all that was perceived as being needed, began to take shape, component by component, tool by tool. Eventually the various concepts were condensed into three basic tools, Capsules A, B and C, and additional supporting technology and infrastructure, that when ultimately developed and implemented as a system, should address the immediate need to serve a creditable initial systems approach to introduce gut in vivo technology.

SUMMARY OF THE INVENTION

A comprehensive system for gut in vivo exploration, discovery, characterization, research, diagnostics, and treatment comprising three different ingestible apparatuses and their associated methodologies, is invented and under development to provide researchers and medical professionals the tools needed to discover the causes of gut-based illnesses and diseases, treat, and hopefully cure them. The three apparatuses are capsules, each specifically designed to perform fundamental functions when ingested under the care of a patient's physician, or other medical profession orders. As an in vivo health care system, the gut processes of digestion can be analyzed on a very small incremental step by step process from the mouth to the anus as a function of the length of the gut "x" and at any point in time "t", including simultaneous chemical substance sampling and testing, along with the associated microbes. The system accommodates testing of diets and the results in an "as is" condition, or as may be modified by substances delivered to any point x within the GI tract at any time t, and the upstream and downstream results simultaneously measured. This capability greatly broadens the horizon for dietary studies with elimination of thousands of extraneous variables. Likewise, medications, or autoimmune response test substances, antibiotics, or other substances for whatever reason, can be delivered in a prescribed manner to the point of interest and the consequences or results in an interactive mode, immediately and simultaneously sampled and monitored at the delivery point and time.

When used as a System, innumerable subjects and issues of a complex matrix nature can be investigated and treated, which will quickly result in the creation of in vivo gut Big Data, of which little currently exists. Many capabilities of characterizing, analyzing, diagnosing, and treating diseases of the gut are enabled when systems logic and rationale are employed in forming a new perspective of the gut, in context with this System associated new technology capabilities and applications. Of course, diagnosing and treating diseases is the ultimate objective, but not to be undervalued as part of the process leading up to such results, is the quantification and characterization of the basic science and engineering principles involved or prevalent in the primary functions of the gut as a system. The gut is one of the most complex systems that can be imagined, involving coupled, time-dependent processes and variables both at the micro and macro levels and of many disciplines. Utilizing distribution functions of hundreds of variables allows the gut to be raised to levels of abstraction, wherein an entirely new class of methodologies and evolutionary technologies can be considered for any aspects of gut analysis, diagnosis and treatment. Such abstraction/quantitative capabilities can include creation of simulation models for a variety of purposes. The individual capabilities of each Capsule A, B, or C should raise the scientific knowledge level and the medical diagnostic and treatment levels of the gut by orders of magnitude, and with the combined capabilities as a System, another order of magnitude or so. This in vivo System delivers these capabilities, and therefore, should greatly expand the horizon for gut health care, and enable many new technologies, institutions, medical professionals, businesses, and industries for gut applications and opportunities.

The present invention solves the problems discussed above by providing an in vivo gut technology system including new investigative and health care methods and processes, and composed of three individual, stand-alone inventions, that when combined logistically, strategically, and applied in combinations, comprise a synergistic, multidisciplinary system with diversified applications for gut healthcare.

Each of the 3 independent invention Capsules A, B, and C, which make up part of the in vivo gut technology system, can create independent Distribution Functions (DFs or DF) of hundreds of variables as functions of gut length "x" and other variables, and each set of DFA, DF8, and DFc. innate to, and limited to the innate capabilities of, their respective capsules create synergistic system capabilities.

The system and enabled DF and other quantitative capabilities in various combinations can comprise new research methods and processes of gut investigation, and new research tools.

The system-enabled DF and other quantitative capabilities in various combinations can comprise new gut diagnostic methods, processes, and tools for clinical applications by physicians of many medical professional disciplines.

The system-enabled DF and other quantitative capabilities in various combinations can comprise new gut treatment methods, processes, and tools for clinical applications by physicians of many medical professional disciplines with specific patient gut illnesses identified, treated, and results measured at the point of event, and incorporated into a DF and abstract numerical or graphical model where comprehensive reference can be made for any reoccurrence.

The system of the present invention provides capabilities, samples, data, and data reduction and analysis is such manner to actually provide for discovery and disclosure of the causes of gut-based illnesses and diseases, as compared to existing technology capabilities of largely extra body researching, correlating and treating the symptoms.

The system of the present invention can reduce the number of variables normally exceeding, perhaps 10,000 variables, by orders of magnitudes for researchers or clinical physicians, with extraneous variables eliminated and only patient specific variables remaining for comparison by utilizing combinations of Capsules A, B, and C along with results from personal physician prescribed applications, such as, specific point testing, sampling, and data interpretation.

A new In Vivo Gut Technology System (System) comprising new investigative and health care methods and processes, and composed of three individual, stand-alone inventions, that when combined logistically, strategically, and applied in combinations, comprise a synergistic, multidisciplinary system with diversified applications, wherein said capabilities in various combinations comprise new gut Abstraction Methods, Processes, and tools for quantitatively and mathematically representing gut functionality and dysfunction, general behavior, characteristics, healthy and unhealthy, and miscellaneous features in a manner suitable for computer software and hardware applications.

The hardware and software applications can include, but are not limited to, numerical simulation models for numerous applications, passive and interactive diagnostic models and systems, passive and interactive treatment models and systems, and interactive database construction, as well as, model construction for specific illnesses and diseases.

The hardware and software applications can further include, but are not limited to, Applications (APS) for generalized guidance in introduction and development of the new in vivo gut technology System.

The hardware and software applications can include, but are not limited to Applications (APS) for Business Development, Business Management, Warehouse development, Prescription Creation and Management, and Technology Transfer, and incorporating all aspects of hardware and software applications for this new in vivo gut technology introduction and development as may be accommodated by abstraction of gut phenomena associated with said System.

The System can generate not only qualitative or circumstantial, but quantitative proof or disproof of hypotheses for digestion processes, gut functions, dysfunctions and disorders, and causes of illnesses, diseases, and microbe based phenomena. For example, the system can be used to prove or disprove important hypotheses pertaining to effects of various microbes processing gut substances in a cascade manner that may create toxins and autoimmune responses, which can result in discovering the cause of certain gut diseases.

With all combined data from System applications and as a result of System existence, such as all DFA, DFn, and DFc in conjunction with all patient physician and research generated volumes of data over a period of time, sufficient knowledge and data can be generated and accumulated for construction of holistic, quantitative models of the human gut.

A new in vivo gut technology System, comprising new investigative and health care methods and processes, and composed of three individual, stand-alone inventions, that when combined logistically, strategically, and applied in combinations, comprise a synergistic, multidisciplinary System with diversified applications, wherein said capabilities in various combinations comprise an Enabling System foundation and framework process, upon which new gut-based institutions, businesses, and industries can be created.

The System enabling capability results, of necessity, in new higher education multi- and interdisciplinary professional training schools or colleges with specific interdisciplinary curricula designed for this new gut in vivo technology System.

As an enabling technology, the System based higher education institutions offer multi- and interdisciplinary educational degree programs based upon matrix organizational structure for efficiency and effectiveness in communications, multi and interdisciplinary teamwork model development, sharing of equipment and facilities, System reflective course syllabi, and overall results-oriented performance objectives and goals, all in contrast to traditional, obsolete, walls and halls of compartments and departments of isolation organization charts.

The System based institutions are created and so structured for research purposes. The System's new enabling framework embellishes, incorporates, provides for and facilitates application of, and participates in, complementary bionanotechnology, especially sensor development, and the creation of new related spinoff Gut In Vivo System Technologies.

A new Gut Laboratory (GL) enterprise facility and business with potential spinoff technology development is specially designed and created to accept, handle and manipulate System collected samples of chemical substances with accompanying microbes, and preserve them until such time said samples are tested and data collected for said intended System purposes, and said samples are appropriately disposed, and wherein said Laboratory is comprised of new specialized, modified, and adapted instrumentation, such as SEMs, spectrometers, chromatographs, and substantial computer-based detection, testing, pattern recognition, and other instrumentation, as well as, voluminous data processing and analysis.

System combinations of belts, pockets, sensors, provoking or perturbation substances, medications suitably packaged, strategies and methodologies as herein disclosed all together in their entirety, constitute an "n-dimensional" matrix of in vivo gut education, research, diagnostic, and treatment medical healthcare system, upon which entirely new type of warehouse, special substance preparations, special laboratory testing facilities, physician education and specialized training and expertise development, substance prescriptions, distribution, and pharmaceutical-like medical orchestration system, constitute an entirely new multi-disciplinary medical education, gut research methodology, healthcare delivery methodology and system, and new Gut Technology Industries (GTI's), each to be implemented as a part of a comprehensive new gut healthcare delivery system.

DETAILED DESCRIPTION OF INVENTION

This invention represents a goal accomplished through three other component inventions referenced as Inventions 1, 2, 3 and Capsules A, B, C, respectively. That is, the ultimate process or system capabilities was achieved through the invention and initialized development of three capsule devices and methods as being the minimal number of tools and sub-processes required to accomplish the overall goals and capabilities needed to introduce a new in vivo gut technology. In other words, to get to the required point of adequate gut health care delivery, the Capsules A, B, and C apparatuses and associated in vivo methodologies were perceived to be, as in the calculus of variations, the brachistochrone path. Reference as provided above under the title of this invention is made back to the individual detailed descriptions of those three inventions, so that discussion of this Invention 4 can focus on the performance, capabilities, and utilization of the resulting 3-component system as a comprehensive in vivo System with 3 complementary components being used in 3 different stages, phases and roles. Absent any one of these three complementary inventions, the ultimate System capabilities and requirements would be destroyed.

To start with, as a system, Invention 4 accomplishes what many college or university deans or provosts, or research directors, find difficult to achieve. It demands and receives, of necessity, teamwork crosscutting many academic disciplines and branches of science and engineering. The multidisciplinary, macro and micro, dynamic, animate system of thousands of coupled, interdependent variables requires the utmost research methodology. The capabilities of this Invention 4, hereinafter called the In Vivo System, or just "System", now push the development of and demand for complementary emerging technologies and other hi-tech infrastructure. Especially the limiting micro technologies are now under another microscope. So, as a System, the overall impact spans even beyond delivering improved human gut health care, as will be discussed later in more detail. As a System, with gut exploratory, discovery, characterization, diagnostic, and treatment capabilities involving fluids, chemicals, and microbes, with synergistic benefits from each of the contributing complementary components A, B, and C and their respective methodologies, the gut and its manifestations within the body take on different meanings and new perspectives. It now becomes the ultimate challenge and object of research for graduate students, faculty, diverse groups of medical professionals, and private enterprise innovators and entrepreneurs. This System process and collective methodology enables another world to be explored and researched utilizing these new tools, or data generated from them, whether experimentally in humans or other animals, or virtually in an abstract manner. It should become the next research project for the international human microbiome initiative with expedited development of the System. It should broaden the scope of microbes in bioengineering processes, and accelerate biosensor, microsensor, lab-on-a-chip applications, and nano-biosensor development. Thus, the System is a significant catalyst that will create demand and applications for a broad spectrum of new technologies. These are just a few examples of enabling roles the System introduces into our technological society, in addition to gut healthcare.

Capabilities of the System for improving human gut health care fall into many different categories, each with many applications. Some of the innumerable applications are abstracted or cited as examples, as follows:

1. Discovery, isolation and characterization of new aerobes and anaerobes living within the gut
2. Association of chemical substances with species and strains of microbes
3. Determination of microbe associated chemical substances that provoke autoimmune responses
4. Determine variability of 1, 2, and 3, e.g. among patients of different characteristics
5. Determining Distribution Functions (DF) for hundreds of variables in patients of different characteristics, or health conditions. One such subset itself consisting of a long list of DF may include anaerobes of thousands of species/strains as functions of "x" or other variables, in essence creating thousands of detailed gut flora profiles over the entire GI tract. Another such subset may include the gut anoxic environment DF as functions of diet, medications, etc.

Other such subset DF may include:
a) unique patient gut flora profiles based upon innumerable control variables,
b) normal chemical substance compositions DF as part of healthy or unhealthy patients
c) chemical substances compositions DF as isolated and contributed by any one of thousands of microbe species/strains, 6. Using results in 5 above, raise the gut to an even higher level of abstraction involving a multitude of variables and conduct computer simulations for a variety of purposes.
7. Verification or rejection, with conclusive evidence, of hypotheses as to the roles bacteria play in the digestive process, or specific illnesses, such as Celiac, gluten sensitivities, or allergies.
8. Addition of new onboard chip-based technologies, especially lab-on-a-chip based technologies, as enabled by the basic Capsules design and capabilities, with intelligence based components, most assuredly will result in major gut disease breakthroughs during the first year of usage.

In other words, there is a virtually endless list of enabled studies and applications involving thousands of variables individually and in combinations for research, patient diagnosis, and patient treatment when pursued with said System. It is quite significant that this System will readily generate so-called Big Data, for the gut, wherein very little site specific in vivo data currently exists on the gut, especially for the most important inaccessible portions of the jejunum and upper colon.

In summary, culmination of all contributions of Capsules A, B and C and all of the raw and calculated data created should result in sufficient information to allow, using Big Data in conjunction with other conventional scientific characterization and modeling methodologies, the creation of comprehensive, holistic models of the human gut system. This system should elevate the scientific level of knowledge of the gut as a system and its associated diseases by orders of magnitude. More importantly, this System should result in major breakthroughs of determining the causes and hopefully curing some of the major gut diseases within the first year of application. Likewise, the enabling capabilities created by this System for family physicians, specialists, and the multitude of health care professionals, clinics, hospitals, and the pharmaceutical industries are enormous.

Finally, it is noteworthy to put into perspective the trillion or more microbes in the GI tract, probably exceeding 10,000 species/strains and all of the process variables they constitute, and then the combinatorial, factorial, combinations and permutations possibilities for isolating just basic cause and effect relationships! A methodology of statistically correlating extra body symptoms of illnesses and diseases or conducting narrow mono-disciplinary research as a means of isolating the causes of gut diseases would appear preposterous, and to date after 2,000 years, this has not been refuted. Then putting into perspective the herein invented in vivo technology, and how at least thousands of variables and millions of combinations are eliminated, so that tractable solution methodology can be used to isolate gut diseases should be of real significance, and a very high priority to develop within the United States of America. The Mayo Clinic estimates that over three billion dollars are spent on over-the-counter antacids, laxatives, acid blockers and fiber supplements alone for indigestion, not including prescriptions or serious diseases. The need for solutions to gut problems is among the world's greatest in healthcare, and this System is designed to have a major impact in a holistic manner.

What is claimed is:

1. A method for diagnosing or treating disease associated with a gut or intestinal tract, comprising:
    collecting samples of gut microbiota from along an intestinal tract of a patient, wherein collecting samples of gut microbiota from along an intestinal tract of a patient comprises:
        providing a first capsule configured to be swallowed and passed through the intestinal tract of the patient, wherein the first capsule comprises:
            a housing defining an opening adapted to allow the samples to pass into the housing,
            a belt disposed within the housing and defining a plurality of indentations, wherein each of the indentations has a volume configured to collect the samples,
            a motor disposed within the housing and configured to drive the belt for collecting the samples at a predetermined rate as the first capsule passes through the intestinal tract; and
        inserting the first capsule into the gastrointestinal tract of the patient;
    perturbing the intestinal tract of the patient; and
    obtaining a response of the perturbing the intestinal tract of the patient.

2. The method of claim 1, further comprising:
    at least one of diagnosing or treating the patient based on the obtained response.

3. The method of claim 1, further comprising:
    analyzing the samples collected by the first capsule to generate at least one of a profile of the intestinal tract of the patient or a composition of the intestinal tract of the patient.

4. The method of claim 1, wherein the perturbing the intestinal tract of the patient comprises:
    providing a second capsule configured to be swallowed and passed through the intestinal tract of the patient, wherein the second capsule comprises:
        a second housing defining an opening adapted to allow samples to pass into and out of the housing,
        at least one sensor transducer,
        a second belt disposed within the second housing and defining a plurality of indentations, each of the indentations having a volume configured to collect or dispense the samples, and
        a second motor or actuator disposed within the second housing, inserting the second capsule into the intestinal tract of the patient.

5. The method of claim 1, further comprising:
    wherein collecting samples of gut microbiota from along the intestinal tract of a patient comprises collecting with the first capsule, and wherein
    perturbing the intestinal tract of the patient comprises perturbing with a second capsule.

6. The method of claim 5, further comprising:
    wherein at least one of diagnosing or treating the patient is performed with the assistance of a third capsule.

7. The method of claim 5, further comprising:
    wherein at least one of diagnosing or treating the patient is based on the use of a third capsule.

8. The method of claim 1, further comprising:
    analyzing the samples collected to generate at least one of a profile of the intestinal tract or a composition of the intestinal tract.

9. The method of claim 1, further comprising:
    recording data associated with at least one of the samples collected and the obtained response in a database.

10. The method of claim 1, wherein collecting samples of gut microbiota from along the intestinal tract of the patient comprises simultaneously collecting chemical substances, including byproducts of said microbiota, at a predetermined time or position from along the intestinal tract of the patient.

11. A system for medical research, diagnosis and treatment associated with diseases, the system comprising:
    a first capsule configured to be swallowed and passed through the intestinal tract, wherein the first capsule comprises:
        a housing defining an opening adapted to allow the samples to pass into the housing,
        a belt disposed within the housing and defining a plurality of indentations, each of the indentations having a volume configured to collect the samples, and
        a motor disposed within the housing and configured to drive the belt for collecting the samples at a predetermined rate as the capsule passes through the intestinal tract, wherein the first capsule acquires samples along an intestinal tract to obtain information at time (t1);
    a second capsule configured to be swallowed and passed through the intestinal tract, wherein the second capsule comprises:

a housing defining an opening adapted to allow substances to pass into and out of the housing, at least one sensor transducer, at least one belt disposed within the housing and defining a plurality of indentations, each of the indentations having a volume configured to perform at least one of collecting and dispensing the samples of matter, and at least one of a motor and an actuator disposed within the housing, wherein the second capsule performs at least one of perturbing, measuring or dispensing substances along an intestinal tract to obtain information at time (t2); and a database configured to store at least the information provided at time t1 and time t2.

12. The system of claim 11, further comprising:

wherein the information stored in the database comprises data associated with at least one of the following:
(a) specific strains of microbes which are correlated with specific symptom combinations,
(b) specific strains of microbes which are correlated with specific chemical substances,
(c) specific strains of microbes which are correlated with specific human diseases,
(d) specific symptoms which are correlated with specific chemical substances,
(e) specific symptoms which are correlated with specific human diseases, and
(f) specific chemical substances which are correlated with specific human diseases.

13. The system of claim 12, wherein, the data associated with at least one (a) through (f) can be used in various combinations as a response to enable the system to experiment, discover, research, develop and apply remediation measures or medications to eliminate an abnormal or diseased patient.

14. A method of diagnosing and treating disease of a patient, comprising:

obtaining baseline information at time (t1) about a patient's gut condition by:
(a) providing a capsule configured to be swallowed and passed through a patient's intestinal tract for obtaining samples of gut microbiota, wherein the capsule comprises:
a housing defining an opening adapted to allow the samples to pass into the housing;
a belt disposed within the housing and defining a plurality of indentations, each of the indentations having a volume configured to collect the samples, and
a motor disposed within the housing and configured to drive the belt for collecting the samples at a predetermined rate as the capsule passes through the intestinal tract;
(b) inserting the capsule into the gastrointestinal tract; and
(c) analyzing the collected samples to determine the composition of the intestinal tract;

obtaining information about the patients' gut condition at time (t2), wherein t2 occurs after t1, and further wherein the information is obtained by:
(a) providing a second capsule configured to be swallowed and passed through a patient's intestinal tract for obtaining samples of gut microbiota, wherein the second capsule comprises:
a second housing defining an opening adapted to allow the samples to pass into the second housing;
a second belt disposed within the second housing and defining a plurality of indentations, each of the indentations having a volume configured to collect the samples, and
a second motor disposed within the second housing and configured to drive the second belt for collecting the samples at a predetermined rate as the second capsule passes through the intestinal tract;
(b) inserting the second capsule into the gastrointestinal tract; and
(c) analyzing the collected samples to determine the composition of the intestinal tract; and
comparing the information obtained at time t2 to the baseline information obtained at time t1.

15. The method of claim 14, further comprising:

generating a database comprising the baseline information obtained at time t1 and the information obtained at time t2.

16. The method of claim 15, wherein the database is associated with discovery, isolation and characterization of new aerobes and anaerobes living within the gut.

17. The method of claim 15, wherein the database is associated with correlations of chemical substances with species and strains of microbes.

18. The method of claim 15, wherein the database is associated with indications of microbe associated chemical substances that provoke autoimmune responses.

19. The method of claim 15, wherein the database is associated with generating distribution functions (DF) for variables in a plurality of patients of different characteristics, or health conditions.

20. The method of claim 19, wherein the distribution functions (DF) comprise species or strains of anaerobes according to a function so to create detailed gut flora profiles over the entire gastrointestinal tract.

21. The method of claim 19, wherein the distribution functions (DF) comprise the gut anoxic environment as functions of diet or medications.

22. The method of claim 19, wherein the distribution Functions (DF) comprise at least one of:
a) unique patient gut flora profiles based upon innumerable control variables,
b) normal chemical substance compositions as part of healthy or unhealthy patients, and
c) chemical substances compositions as isolated and contributed by any one of thousands of microbe species or strains.

23. The method of claim 15, further comprising:

obtaining information about the patients' gut condition at time (t3), wherein t3 occurs after t1 and t2, and further wherein the information is obtained by:
(a) providing a third capsule configured to be swallowed and passed through a patient's intestinal tract for obtaining samples of gut microbiota, wherein the third capsule comprises:
a third housing defining an opening adapted to allow the samples to pass into the third housing;
a third belt disposed within the third housing and defining a plurality of indentations, each of the indentations having a volume configured to collect the samples, and
a third motor disposed within the third housing and configured to drive the third belt for collecting the samples at a predetermined rate as the third capsule passes through the intestinal tract;
(b) inserting the third capsule into the gastrointestinal tract; and (c) analyzing the collected samples to determine the composition of the intestinal tract; and comparing the information obtained at time t3 to the information contained in the database.

24. The method of claim 23, further comprising:

generating at least one of a diagnosis or a treatment for the patient based on the comparison of the patient's information at time t3 to the information in the database.

\* \* \* \* \*